United States Patent
Jalde

(10) Patent No.: US 6,192,885 B1
(45) Date of Patent: Feb. 27, 2001

(54) METHOD FOR CONTROLLING AN EXPIRATORY VALVE IN A VENTILATOR

(75) Inventor: Fredrik Jalde, Stockholm (SE)

(73) Assignee: Siemens-Elema AB, Solna (SE)

( * ) Notice: Subject to any disclaimer, the term of this patent is extended or adjusted under 35 U.S.C. 154(b) by 0 days.

(21) Appl. No.: 09/333,712

(22) Filed: Jun. 15, 1999

(30) Foreign Application Priority Data

Jul. 6, 1998 (DE) .............................................. 198 30 164
Jun. 15, 1998 (SE) ..................................................... 9802121

(51) Int. Cl.⁷ ...................................................... A62B 9/02
(52) U.S. Cl. ............................... 128/205.24; 128/204.21; 128/204.18
(58) Field of Search ......................... 128/204.21, 204.18, 128/205.24

(56) References Cited

U.S. PATENT DOCUMENTS

| 4,611,591 | 9/1986 | Inui et al. . |
| 5,002,050 | * 3/1991 | McGinnis ........................ 128/204.18 |
| 5,072,729 | 12/1991 | DeVries . |
| 5,572,993 | * 11/1996 | Kurome et al. .................. 128/204.23 |

FOREIGN PATENT DOCUMENTS 293 268   8/1991 (DE) .

* cited by examiner

*Primary Examiner*—John G. Weiss
*Assistant Examiner*—Mital Patel
(74) *Attorney, Agent, or Firm*—Schiff Hardin & Waite

(57) ABSTRACT

In a method for controlling an expiratory valve in a ventilator during expiration, the expiratory valve is opened substantially fully for a first interval. Fully opening the expiratory valve has the advantage of minimizing the expiratory resistance a patient needs to overcome. Keeping the expiratory valve open as long as possible during expiration, without losing control of positive end expiratory pressure (PEEP), is therefore advantageous. An optimal system is achieved. In a method wherein pressure in the expiratory section of the ventilator is measured during a second interval, the expiratory valve is regulated so a predetermined end pressure is obtained in the expiratory section, and at least one parameter, directly or indirectly related to control of the expiratory valve, is determined, and a determination is made from that parameter as to whether the next first interval for the next expiration should be longer than, shorter than or as long as the first interval.

9 Claims, 2 Drawing Sheets

METHOD FOR CONTROLLING AN EXPIRATORY VALVE IN A VENTILATOR

BACKGROUND OF THE INVENTION

1. Field of the Invention

The present invention relates to a method for controlling an expiratory valve in a ventilator.

2. Description of the Prior Art

In normal circumstances in respiratory care, the patient is allowed to exhale as normally as possible, sometimes against an elevated positive end expiratory pressure (PEEP). The tubes (the tracheal tube in particular) and devices (e.g. a dehumidifier, bacterial filter and the ventilator's expiratory valve in particular) in the path of flow of expired gas pose a resistance to expiration. The patient is forced to overcome this unnatural resistance, which can become tiring.

One way to reduce such resistance is to open the expiratory valve to a maximum for a specific period of time. East German Patentschrift 293 268 describes one such method for controlling a ventilator, wherein the expiratory valve consists of an on/off valve with only two positions, fully open or fully closed.

This known control of the expiratory valve causes the expiratory valve to open at the onset of expiration. It is kept open for a specific period of time and then closed. The pressure (end pressure) on the valve (on the patient side) then corresponds to the pressure in the patient's lungs. The period of time in which the valve is kept open for the next consecutive breathing cycles is set according to the difference between the determined end pressure (actual value) and a preset value for PEEP (reference value). The time the valve is kept open is increased if the measured value exceeds the reference value. The time the valve is kept open is reduced if the measured value is less than the reference value. In this way, a convergence toward the reference value is obtained.

A disadvantage of this known control system is that the patient risks exposure to an end pressure that is less than PEEP during an initial phase of treatment (when maintenance of PEEP is particularly important in preventing the collapse of alveoli in the lungs)

Another disadvantage of this known control system is that the patient is subjected to varying end pressures, at least during the adjustment phase of treatment, since an end pressure greater than the target PEEP pressure could develop.

An additional disadvantage of this known control system is that the patient's lungs and the tubing do not constitute a static system. Any change in the patient's physical position could alter parameters for the gas mechanics of the lungs/tubing system, for which the control system is unable to compensate. In a worst case scenario, this could result in an end pressure much lower (or higher) than the reference value.

Yet another disadvantage is the fact that bias flows cannot be used, since the known valve is an on/off valve. Bias flows have the advantage of making flow-triggering possible for the patient.

SUMMARY OF THE INVENTION

An object of the present invention is to provide a method for controlling an expiratory valve in a ventilator during expiration wherein the aforementioned problems are avoided.

The above object is achieved in accordance with the principles of the present invention in a method for controlling an expiratory valve in a ventilator during expiration, wherein the expiratory valve is open substantially completely in a first interval and wherein, during a second interval following the first interval, pressure is measured in the expiratory system of the ventilator, the expiratory valve is controlled so that a predetermined end pressure is achieved in the expiratory section including determining at least one parameter, directly or indirectly related to control of the expiratory valve, and determining from that parameter whether the duration of the next-following first interval for the next expiration should be longer than, shorter than, or the same as the duration of the first interval during the current expiration.

The valve can be kept fully open during a first interval by the use of an adjustable expiratory valve and then regulated toward a reference value (PEEP) during a second interval when expiration has largely subsided. A parameter related in some way to control of the expiratory valve is determined and utilized for establishing the first interval for the next expiration. Flow through the expiratory valve is one such parameter, as are the required regulatory force on or the regulatory current to the expiratory valve in achieving the preset end pressure (PEEP). Pressure is also one such parameter, of course.

It should be clearly noted that, in contrast to an on-off valve, "fully open" as used in the context of the valve according to the invention means sufficiently open to avoid the resistance to gas flow that the valve causes during control of PEEP. Whether this requires the valve to be truly fully open or only open to a certain degree (50%, 70% or other degree) depends more on the physical properties (flow through area, etc.) of the valve than the control function (to which the invention is directed to).

To prevent development of an unstable system, a known integration-type control method can be used over a number of breathing cycles. A specific number of preceding expirations then serve as the basis (average value formation) for determining whether the next first interval should be prolonged or reduced.

If the first interval is too long and the end pressure is too low at the start of the second interval, the correct end pressure (PEEP) could still be achieved during expiration as the result of an existing bias flow of breathing gas. Such bias flows are known and used for e.g. the flow triggering function in the Servo Ventilator 300, Siemens-Elema AB, Sweden. If no bias flow is employed or if it is insufficient to produce the desired end pressure, a supplementary flow of breathing gas can be supplied.

The duration of the first interval can advantageously be maximized to e.g. 0.5 second.

DESCRIPTION OF THE PREFERRED EMBODIMENTS

Figure 1:
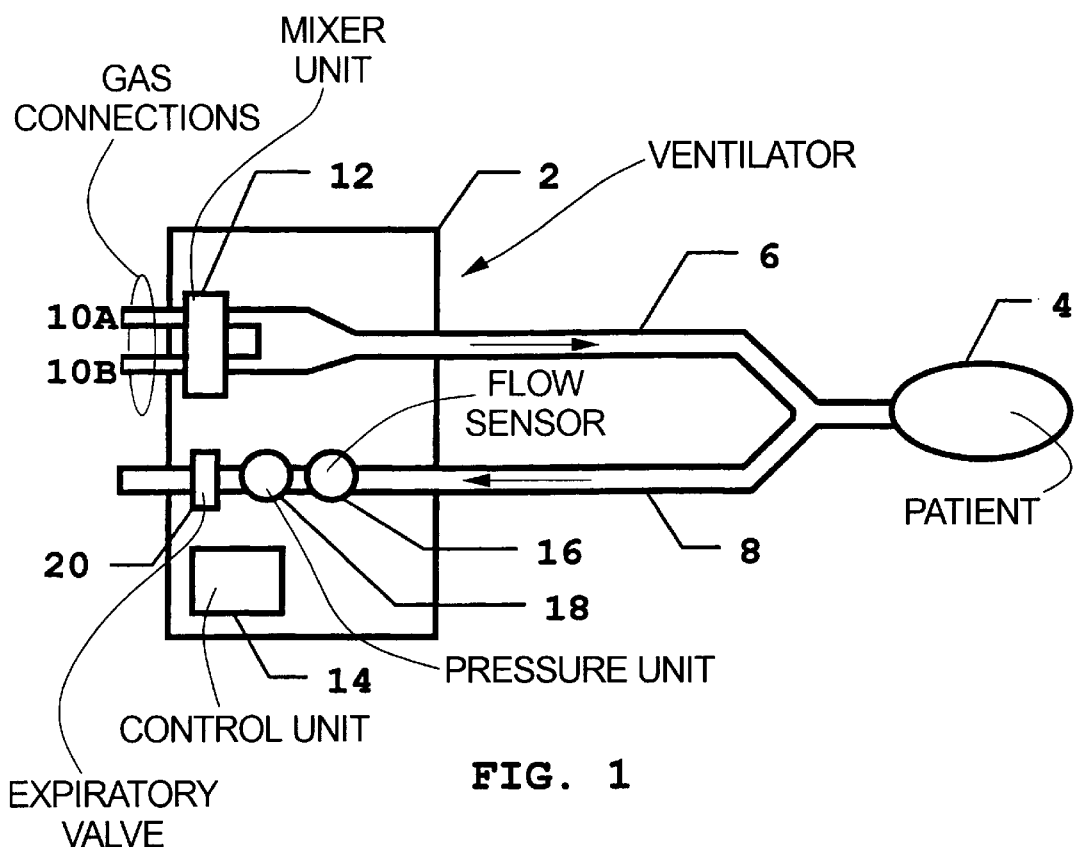
FIG. 1 is a schematic illustration of a ventilator, in which the method according to the invention can be implemented.

FIG. 1 shows a ventilator 2, connected to a patient 4, for providing respiratory care. Breathing gas is carried to the patient 4 during inspiration in an inspiration line 6 and back to the ventilator 2 during expiration in an expiratory line 8.

The breathing gas is mixed from gases supplied to the ventilator 2 through a first gas connection 10A and a second gas connection 10B. A mixer unit 12 regulates each gas with respect to pressure and flow so the mixed final breathing gas has the pressure and flow set by the physician. The mixer unit 12, which contains e.g. valves, is controlled by a control unit 14 in the ventilator 2. The mixer unit 12 can also be regulated to supply a continuous bias flow of breathing gas during expiration in addition to the inspiration flow of gas.

Expired breathing gas passes a flow sensor 16 and a pressure 5 sensor 18 in the expiratory section of the ventilator 2 before it is discharged into the atmosphere through an expiratory valve 20. Measurement signals are sent to the control unit 14 which controls the expiratory valve 20.

The control unit 14 controls the expiratory valve 20 so that the expiratory valve 20 is sufficiently open for a first interval during expiration in order to minimize expiratory resistance. A second interval then commences during which the expiratory valve 20 is regulated so the system achieves a preset end expiratory pressure (PEEP) at the end of expiration. This end pressure is an over-pressure in relation to prevailing atmospheric pressure and can vary upwardly from 0 cmH$_2$O.

In the transition to or during the second interval, a parameter, directly or indirectly related to regulation of the expiratory valve 20, is determined. The pressure measured by the pressure sensor 18 is one such parameter, as is the flow measured by the flow sensor 16. Other parameters are the regulatory force on the expiratory valve 20 or the regulatory current to the expiratory valve 20. The latter parameter is obviously only applicable to an expiratory valve 20 which displays a relatively simple correlation between force and current.

The control unit 14 then utilizes the established parameter for determining whether the expiratory valve 20 should be kept fully open for a shorter, longer or equally long period of time in the next expiration. The determination can be made from one or a number of breathing cycles. A number of breathing cycles, combined with an integrative control mode, makes the system stable and safe.

Figure 2:
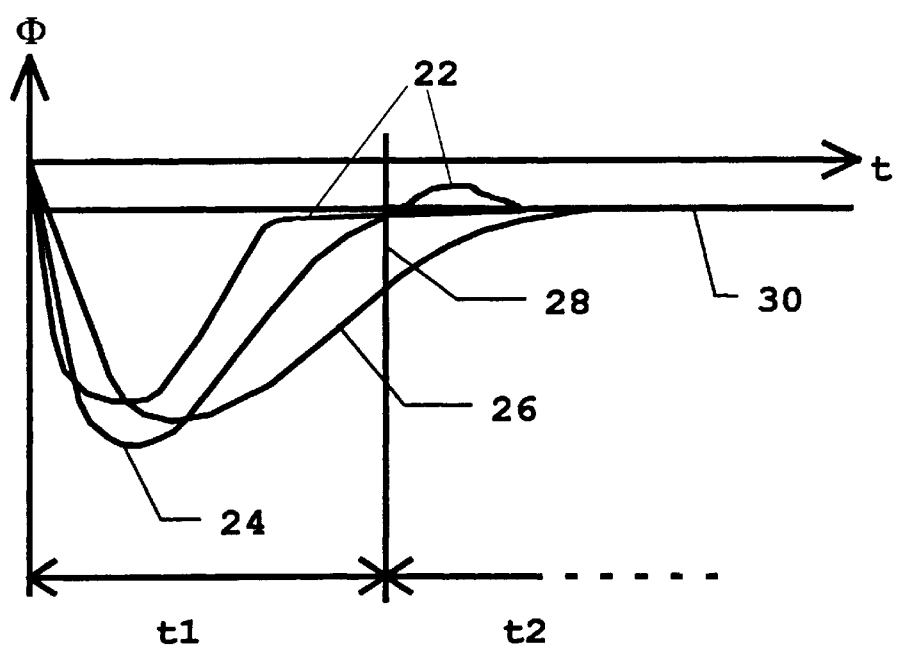
FIG. 2 is a diagram showing the use of flow as a parameter in the method according to the invention.
Figure 3:
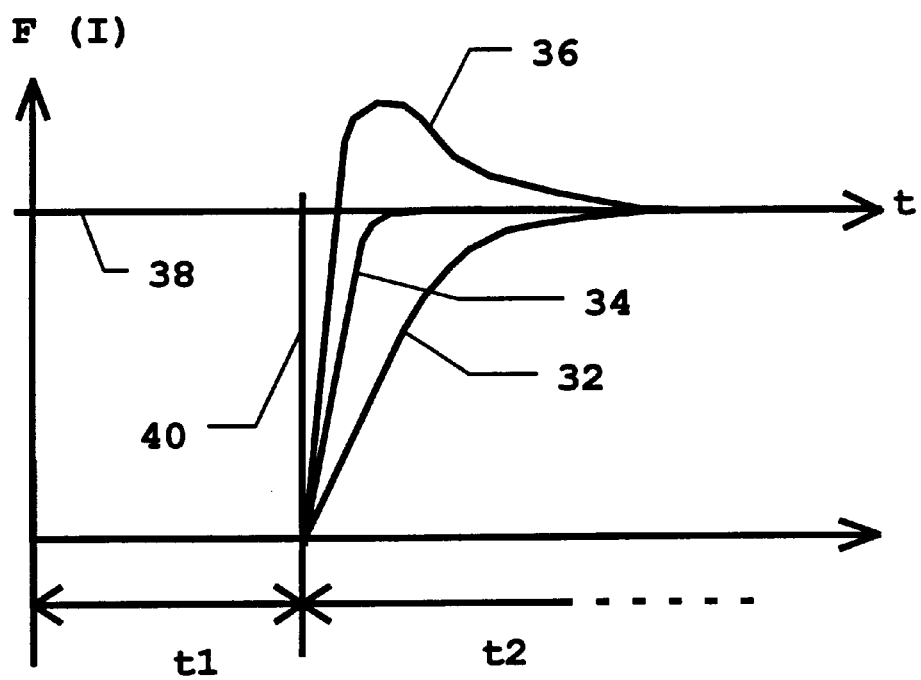
FIG. 3 is a diagram illustrating the use of regulatory force as a parameter in the method according to the invention.
Figure 4:
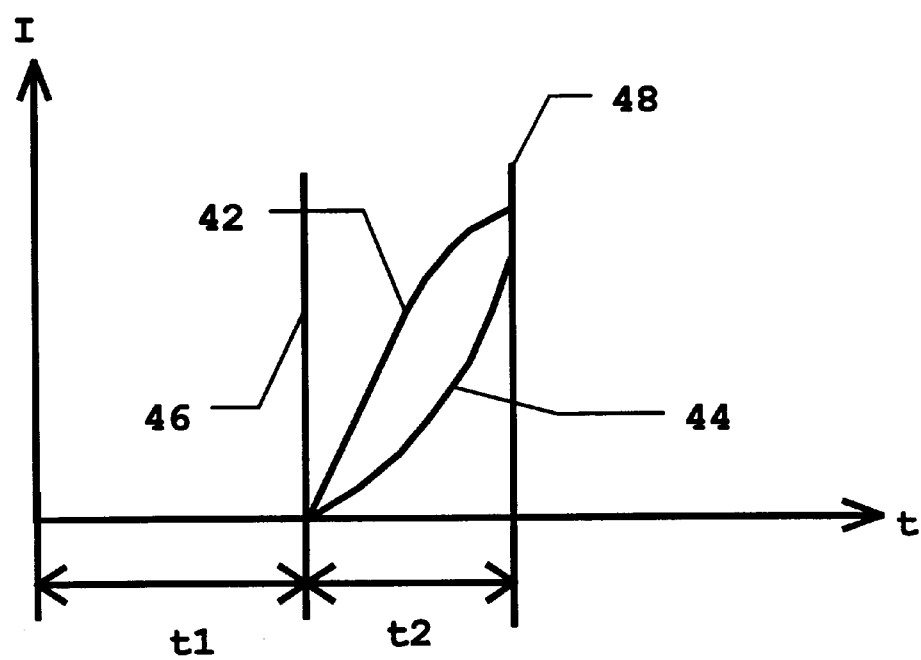
FIG. 4 is a diagram illustrating the use of regulatory current as a parameter in the method according to the invention.

FIGS. 2, 3 and 4 are diagrams illustrating the way in which three different parameters can be used for determining the first interval for the next expiration.

FIG. 2 shows flow as a function of time during expiration. Flows are depicted here as being negative, since the nomenclature usually designates flows to the patient as positive. A first curve 22, a second curve 24 and a third curve 26 show three possible flow sequences during expiration in relation to the method according to the invention. A vertical line 28 designates the end of the first interval ti, during which the expiratory valve is sufficiently open, and the start of the second interval t2, during which the expiratory valve is controlled so the preset end pressure is achieved. The duration of the second interval t2 is mainly controlled by the difference between the preset expiratory duration and t1. In all normal conditions, this leaves enough time to achieve the correct end pressure. The duration of t2 will be governed by the time it takes the system to achieve the correct end pressure only in specific circumstances. The horizontal line 30 designates the level of a bias flow that is always present during expiration (and which can even be 0, i.e. no flow at all).

The first curve 22 designates a situation in which the first interval ti is too long, i.e. the expiratory valve stays open too long. Flow before the end of the first interval ti (the vertical line 28) has dropped to the level of the bias flow 30. The pressure is then less than the preset end pressure. In this situation, the expiratory valve can be fully closed, and the bias flow causes the pressure to rise toward the preset end pressure. If the valve is not fully closed, it will take longer time to build up the pressure.

In the method according to the invention, it is determined that the next first interval in the next expiration will be shorter. In a control context, this can be accomplished by reductions in specific steps, a reduction to the duration the first interval ti should have had (i.e. up to the intersection of the first curve 22 and the bias flow 30) or an averaged duration for a number of preceding breathing cycles. Known conventional control methods can be used here.

Certain safety features can be incorporated into the control system in order to keep pressure in any part of the first interval ti from dropping too far below the preset end pressure.

One such safety feature is to limit the longest duration of the first interval ti, e.g. to a maximum of 0.5 second. Excessive amounts of breathing gas then will not have time to flow out of the patient.

Another safety feature is to measure flow throughout an entire expiration (as is common) and to terminate the first interval ti prematurely if flow drops to the level of the bias flow 30. A safety margin can also be incorporated, for example the first interval t1 can be terminated if the measured flow drops to a certain level, e.g. 20% above the level of bias flow 30.

Combinations of the two safety features are obviously possible.

The second curve 24 illustrates a situation in which the first interval t1 has been regulated to the correct duration. In principle, flow reaches the level of bias flow 30 at the same time the first interval ti elapses. The expiratory valve then mainly regulates bias flow only, and the end pressure (pressure in the patient's lungs) is, in principle, the end pressure previously set. This is the situation the control method strives to achieve, and it is maintained with great accuracy in relatively constant breathing cycles.

Finally, the third curve 26 describes a situation in which the first interval ti is too short. Flow in the third curve 26 has not yet dropped to the level of bias flow 30, and pressure in the patient's lungs is higher than the preset end pressure. The expiratory valve is kept open more than needed to regulate the bias flow 30 in order to discharge more breathing gas, thereby making it possible to maintain the preset end pressure.

In the corresponding manner described above, the next first interval for the next expiration is prolonged. The magnitude of this prolongation can be preset or calculated from one or a number of breathing cycles according to normal automatic control theory.

A number of additional features can be incorporated to keep expiratory resistance from becoming unnecessarily high, i.e. control of the expiratory valve starts too soon. One such feature is to exercise overriding control that prolongs (or shortens if necessary) the time at which the first interval t1 elapses. This control can be based on measured flow. For example, if flow at the end of the first interval t1 is more than e.g. 200% of the bias flow, the first interval t1 is prolonged by a preset increment.

As an alternative to manipulating the first interval t1, the expiratory valve can be regulated to remain fully open for the second interval as long as the flow exceeds bias flow 30 by a sufficient degree.

Flow is not the only parameter that indicates whether the first interval t1 is too long, too short or about right. Pressure can be measured immediately after control of the expiratory valve starts. The measured pressure value then indicates whether the first interval t1 needs to be changed. Regulation to the desired end pressure is performed with the aid of the measured pressure. Flow in the first interval t1 can then be measured and used for the supplementary features above.

An additional parameter is indicated in the diagram in FIG. 3. A first curve 32, a second curve 34 and a third curve 36 illustrate three typical situations for the requisite regulatory force on the expiratory valve in the transition to control in the second interval t2. A horizontal line 38 designates the regulatory force required to maintain the bias flow of breathing gas passing the expiratory valve. A vertical line 40 designates the transition between the first interval t1 and the second interval t2.

The first curve 32 illustrates a situation in which the first interval was too short. The slow change in the regulatory force required by the expiratory valve indicates that the pressure exceeds the preset end pressure and that a certain amount of breathing gas needs to be discharged from the system.

The second curve 34 illustrates a situation in which the first interval was proper. Regulatory forces increase relatively steeply but without overshoot.

The third curve 36 illustrates a situation in which the first interval was too long. Heavy overshoot in requisite force indicates that the pressure dropped below the preset end pressure and that a pressure build-up by means of bias flow is necessary.

Determination of the next first interval for the next expiration can be made in a manner analogous to the procedure outlined in the description of FIG. 2. The introduction of safety features based on flow etc. is also possible here.

A diagram in FIG. 4 describes another parameter, viz. requisite current. In contrast to the examples above, this example requires the use of an electrically operated expiratory valve employing e.g. a traction magnet. The required current is then largely proportional to the requisite force described in FIG. 3. The curves 32, 34, 36 in FIG. 3 can therefore also be said to correspond to the current in the various situations. Signal processing can be performed in such a way that the various situations arising can be identified by e.g. comparison of the signal level at the first change in sign for the derivative of the required current with the level of the requisite current at the time t2 elapses (curve morphology has been idealized somewhat in FIG. 3)

FIG. 4 illustrates further alternative curve morphologies occurring, viz, a fourth curve 42 and a fifth curve 44 which illustrate situations in which a first expiratory interval ti too short and too long respectively. These curve morphologies are mainly found at fast breathing rates. A first vertical line 46 designates the transition from the first interval ti to the second interval t2. A second vertical line 48 designates the end of the second interval.

The fourth curve 42 illustrates a situation in which the first interval ti was too short. If this curve morphology is registered without registration of any of the curves according to FIG. 3 and the duration of the first interval ti is less than the maximum permissible duration, this duration can be increased. The end derivative of the fourth curve 42 can be used for determining the increase. Alternately, the variance between measured pressure and end pressure can be determined and used for determination of the increase.

In the corresponding manner, the fifth curve 44 illustrates a situation in which the first interval t1 was too long. Even here the end derivative and the maximum permissible duration for the first interval ti can be used for determination of the decrease. Alternately, the variance between measured pressure and end pressure can be determined and also used for determination of the decrease.

Even in the situation in which current is used as a parameter, the aforementioned safety and control functions can be utilized in both the first interval and the second interval. Combinations of the various embodiments, in which a number of criteria and parameters are weighed together in determining the duration of a next first interval, are possible.

The parameter can even be other signals in the control system to the extent that they reflect e.g. force or current. A control signal reflecting requisite current is therefore one conceivable parameter, as is requisite current itself.

The ventilator in FIG. 1 illustrates only one type of ventilator to which the method according to the invention can be applied. But 'ventilator' also refers to other devices for supplying breathing gas, such as respirators and anesthetic machines.

Although modifications and changes may be suggested by those skilled in the art, it is the intention of the inventor to embody within the patent warranted hereon all changes and modifications as reasonably and properly come within the scope of his contribution to the art.

I claim as my invention:

1. A method for controlling an expiratory valve in a ventilator during expiration, said expiratory valve being disposed in an expiratory section of the ventilator, comprising the steps of:

substantially completely opening said expiratory valve for a first interval, having a duration, in a first expiration;

during a second interval following said first interval in said first expiration, measuring pressure in said expiratory section of said ventilator;

during said second interval, controlling said expiratory valve to produce a predetermined end pressure in said expiratory section;

identifying at least one parameter related to controlling said expiratory valve in said second interval; and in said second interval, determining from said parameter whether a duration of a first interval in a next-following, second expiration relative to the duration of said first interval in said first expiration.

2. A method as claimed in claim 1 comprising the step of measuring flow through said expiratory valve in said second interval to obtain a measured flow value, and using said measured flow value as said parameter.

3. A method as claimed in claim 1 comprising identifying a regulatory force on said expiratory valve required to achieve said predetermined end pressure in said second interval, and using said regulatory force as said parameter.

4. A method as claimed in claim 1 wherein the step of controlling said expiratory valve comprises supplying a regulatory current to said expiratory valve in said second interval to produce said predetermined end pressure, and measuring said regulatory current, and using said regulatory current as said parameter.

5. A method as claimed in claim I comprising identifying a time at which said second interval begins, and using said time as said parameter.

6. A method as claimed in claim 1 comprising the step of identifying any change in the respective first intervals of a plurality of respirations and comparing said change as a check, to any change between the duration of said first interval in said first expiration to the duration of said first interval in said second expiration.

7. A method as claimed in claim 1 comprising limiting the duration of said first interval to a predetermined value.

8. A method as claimed in claim 7 comprising limiting the duration of said first interval to 0.5 seconds.

9. A method as claimed in claim 1 comprising the additional step of controlling said expiratory valve to release a predetermined bias flow throughout said first and second expirations.

* * * * *

UNITED STATES PATENT AND TRADEMARK OFFICE
CERTIFICATE OF CORRECTION

Page 1 of 1

PATENT NO.  : 6,192,885 B1
DATED       : February 27, 2001
INVENTOR(S) : Fredrik Jalde It is certified that error appears in the above-identified patent and that said Letters Patent is hereby corrected as shown below:

Title page,
Item [30], "Foreign Application Priority Data" cancel:
"Jul. 6, 1998   (DE) .....................198 30 164"

Signed and Sealed this

Fifteenth Day of January, 2002

Attest:

JAMES E. ROGAN
*Director of the United States Patent and Trademark Office*

*Attesting Officer*